(12) United States Patent
Jeon et al.

(10) Patent No.: US 10,667,605 B2
(45) Date of Patent: Jun. 2, 2020

(54) BATHROOM MANAGEMENT APPARATUS

(71) Applicant: LG ELECTRONICS INC., Seoul (KR)

(72) Inventors: Jinhyeon Jeon, Seoul (KR); Jeongyun Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 135 days.

(21) Appl. No.: 15/913,154

(22) Filed: Mar. 6, 2018

(65) Prior Publication Data

US 2018/0249830 A1 Sep. 6, 2018

(30) Foreign Application Priority Data

Mar. 6, 2017 (KR) ........................ 10-2017-0028491

(51) Int. Cl.
| | | |
|---|---|---|
| *A47B 67/00* | (2006.01) | |
| *A47B 55/00* | (2006.01) | |
| *A47G 1/16* | (2006.01) | |
| *A47B 81/00* | (2006.01) | |
| *A47B 47/00* | (2006.01) | |
| *H05B 3/84* | (2006.01) | |
| *A61L 2/10* | (2006.01) | |
| *A61L 2/26* | (2006.01) | |
| *A47K 10/06* | (2006.01) | |
| *A47B 96/20* | (2006.01) | |
| *F25D 11/00* | (2006.01) | |
| *A47B 95/00* | (2006.01) | |

(Continued)

(52) U.S. Cl.
CPC ........ *A47B 67/005* (2013.01); *A47B 47/0091* (2013.01); *A47B 55/00* (2013.01); *A47B 81/00* (2013.01); *A47G 1/1653* (2013.01); *A61L 2/10* (2013.01); *A61L 2/26* (2013.01); *H05B 3/845* (2013.01); *A47B 95/008* (2013.01); *A47B 96/20* (2013.01); *A47B 2096/208* (2013.01); *A47G 2001/1673* (2013.01); *A47K 10/06* (2013.01); *A61L 2202/11* (2013.01); *F25B 21/02* (2013.01); *F25D 11/00* (2013.01); *H02J 7/0042* (2013.01)

(58) Field of Classification Search
CPC ........ A47B 67/02; A47B 67/005; H05B 3/845
See application file for complete search history.

(56) References Cited

U.S. PATENT DOCUMENTS

| | | | | |
|---|---|---|---|---|
| 1,941,126 | A | * | 12/1933 | Blackman .............. A47B 67/02 312/329 |
| 2,419,226 | A | | 4/1947 | Palmer |
| 2,598,917 | A | | 6/1952 | Ingram |

(Continued)

OTHER PUBLICATIONS

U.S. Office Action dated Nov. 8, 2019 issued in U.S. Appl. No. 15/913,416.

(Continued)

*Primary Examiner* — Matthew W Ing
(74) *Attorney, Agent, or Firm* — KED & Associates LLP

(57) ABSTRACT

A bathroom management apparatus may be capable of dehumidifying and defrosting a mirror installed at a door. The bathroom management apparatus may include a cabinet having a front side that is open, a door configured to open/close the open front side of the cabinet, a mirror provided at a front surface of the door, and a heater configured to heat the mirror. The heater may be disposed behind the mirror to heat the mirror.

14 Claims, 9 Drawing Sheets

(51) Int. Cl.
  *H02J 7/00* (2006.01)
  *F25B 21/02* (2006.01)

(56) References Cited

U.S. PATENT DOCUMENTS

| | | | |
|---|---|---|---|
| 3,054,194 A | | 9/1962 | Hayes |
| 3,306,689 A | | 2/1967 | Anson |
| 3,515,450 A | | 6/1970 | Jaecke |
| 3,519,318 A | | 7/1970 | Hagen |
| 3,521,936 A | | 7/1970 | Coker, Jr. |
| 3,955,922 A | | 5/1976 | Moulthrop |
| 4,134,625 A | | 1/1979 | Palka |
| 4,189,195 A | | 2/1980 | Turney |
| 4,195,416 A | | 4/1980 | Hall |
| 4,239,310 A | * | 12/1980 | Benjamin ............ A47B 67/005 312/224 |
| 4,644,136 A | | 2/1987 | Watchman |
| 5,108,162 A | | 4/1992 | Lund |
| 5,255,971 A | * | 10/1993 | Aisley ................ A47B 67/02 312/242 |
| 5,355,627 A | | 10/1994 | Katz |
| 5,380,981 A | * | 1/1995 | Feldman ............ H05B 3/845 219/219 |
| 5,444,984 A | | 8/1995 | Carson |
| 5,487,877 A | | 1/1996 | Choi |
| 5,524,980 A | | 6/1996 | Carter |
| 5,577,819 A | | 11/1996 | Olsen |
| 6,089,685 A | | 7/2000 | Ryan |
| 6,365,876 B1 | * | 4/2002 | Park ...................... A47G 1/02 219/219 |
| 6,420,682 B1 | * | 7/2002 | Sellgren ............ H05B 3/845 156/232 |
| 6,525,298 B1 | | 2/2003 | Hunts |
| 6,640,581 B1 | | 11/2003 | Choi |
| 6,664,513 B1 | * | 12/2003 | Park ..................... H05B 3/845 219/219 |
| 6,769,197 B1 | | 8/2004 | Tai |
| 7,083,110 B2 | | 8/2006 | Kim |
| 7,258,606 B1 | | 8/2007 | Reid |
| 7,543,339 B1 | | 6/2009 | Harris |
| 8,166,667 B1 | | 5/2012 | Lora |
| 8,517,478 B2 | | 8/2013 | Diemel |
| 9,013,071 B1 | | 4/2015 | Levi |
| 9,644,834 B2 | | 5/2017 | Cano |
| 2003/0042828 A1 | | 3/2003 | Bonin |
| 2005/0052100 A1 | | 3/2005 | Horning |
| 2005/0167563 A1 | | 8/2005 | Delaney |
| 2005/0264141 A1 | | 12/2005 | Whitall |
| 2006/0272170 A1 | | 12/2006 | Holmes |
| 2007/0278755 A1 | | 12/2007 | Horning |
| 2008/0252189 A1 | | 10/2008 | Regan |
| 2009/0255891 A1 | | 10/2009 | Lanning |
| 2010/0224615 A1 | | 9/2010 | Gallo |
| 2011/0133572 A1 | | 6/2011 | Levi |
| 2012/0074121 A1 | | 3/2012 | Gagas |
| 2014/0210331 A1 | | 7/2014 | Tunzi |
| 2015/0374121 A1 | | 12/2015 | Wood |
| 2016/0211689 A1 | | 7/2016 | Wang |
| 2017/0181541 A1 | | 6/2017 | Stanley, Jr. |
| 2018/0110382 A1 | | 4/2018 | Jeon |
| 2018/0249826 A1 | | 9/2018 | Kim |
| 2018/0249827 A1 | | 9/2018 | Kim |
| 2019/0087788 A1 | | 3/2019 | Murphy |

OTHER PUBLICATIONS

U.S. Notice of Allowance dated Nov. 15, 2019 issued in U.S. Appl. No. 15/913,257.
U.S. Appl. No. 15/913,154, filed Mar. 6, 2018.
U.S. Appl. No. 15/913,257, filed Mar. 6, 2018.
U.S. Appl. No. 15/913,416, filed Mar. 6, 2018.

* cited by examiner

FIG. 6
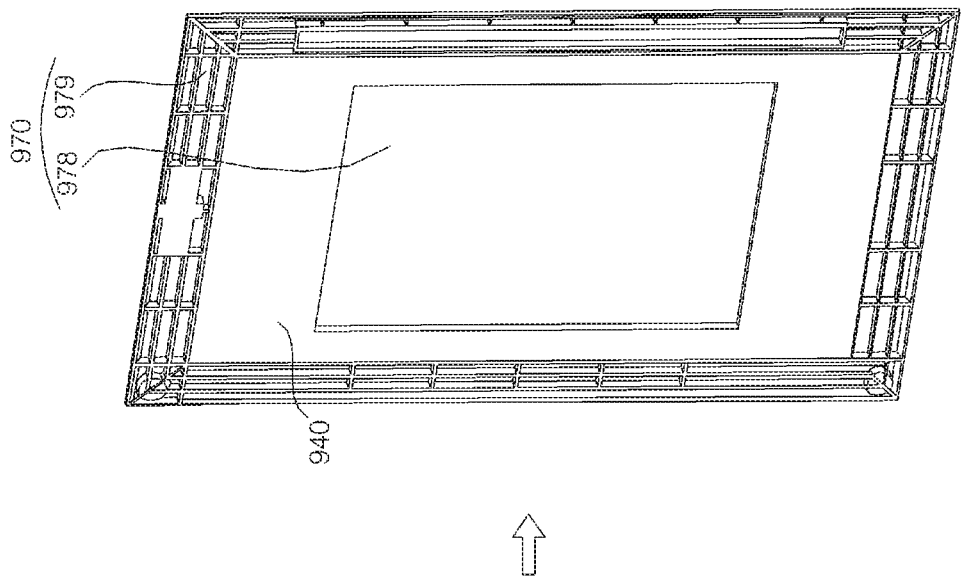
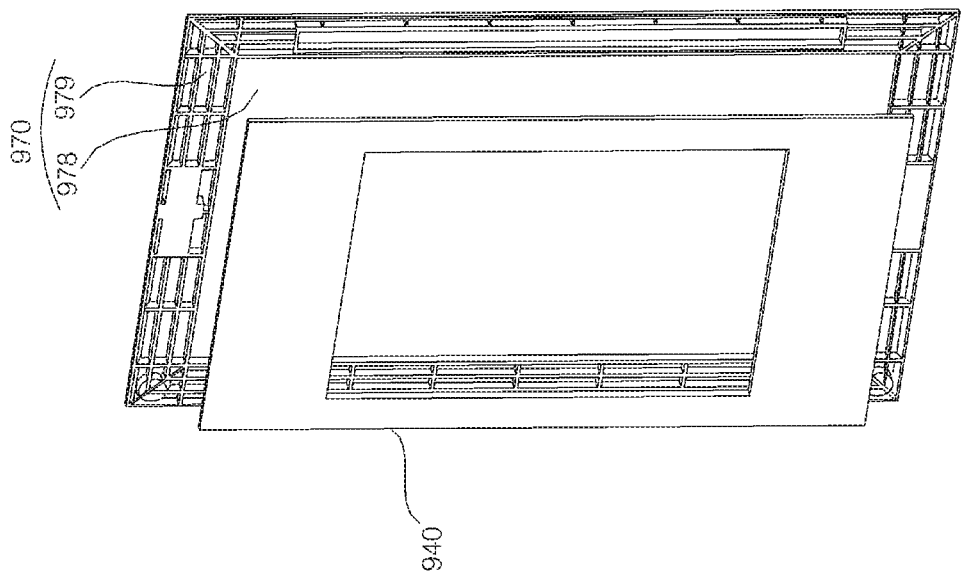

FIG. 9
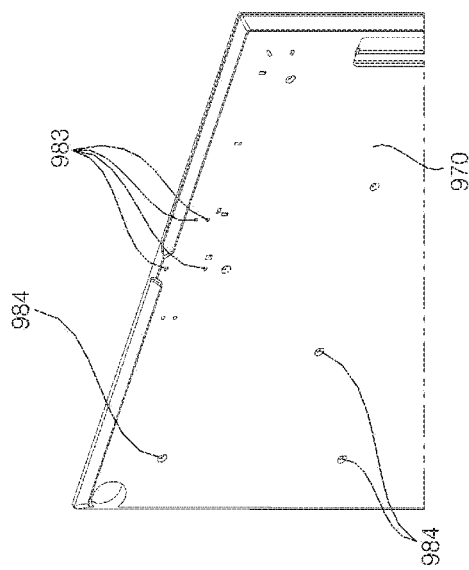
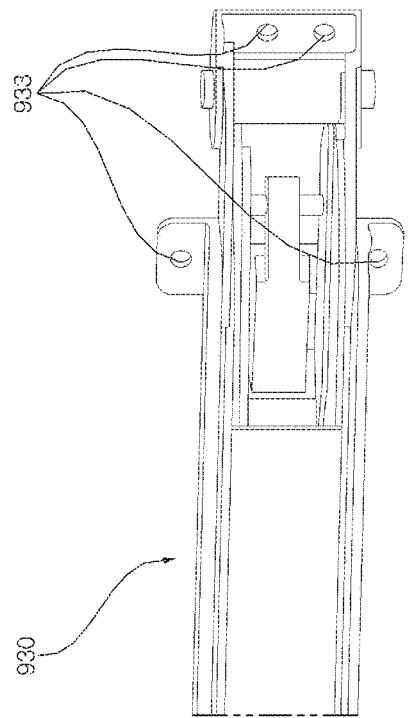

BATHROOM MANAGEMENT APPARATUS

CROSS-REFERENCE TO RELATED APPLICATION(S)

This application claims the priority benefit of Korean Patent Application No. 10-2017-0028491, filed in Korea on Mar. 6, 2017 in the Korean Intellectual Property Office, the disclosure of which is incorporated herein by reference.

U.S. application Ser. Nos. 15/913,154; 15/913,257; and 15/913,416, are related and are hereby incorporated by reference in their entirety. Further, one of ordinary skill in the art will recognize that features disclosed in these above-noted applications may be combined in any combination with features disclosed herein.

BACKGROUND

1. Field

A bathroom management apparatus having functional modules that provide storage space and removes humidity is disclosed.

2. Background

Bathroom management apparatus having functional modules are known. However, they suffer from various disadvantages.

BRIEF DESCRIPTION OF THE DRAWINGS

Embodiments will be described in detail with reference to the following drawings in which like reference numerals refer to like elements, and wherein:

FIG. 6 is a view illustrating a process of coupling an inner frame and an outer frame shown in FIG. 5;

FIG. 9 is a view illustrating a hinge and an outer frame shown in FIG. 5.

DETAILED DESCRIPTION

Figure 1:
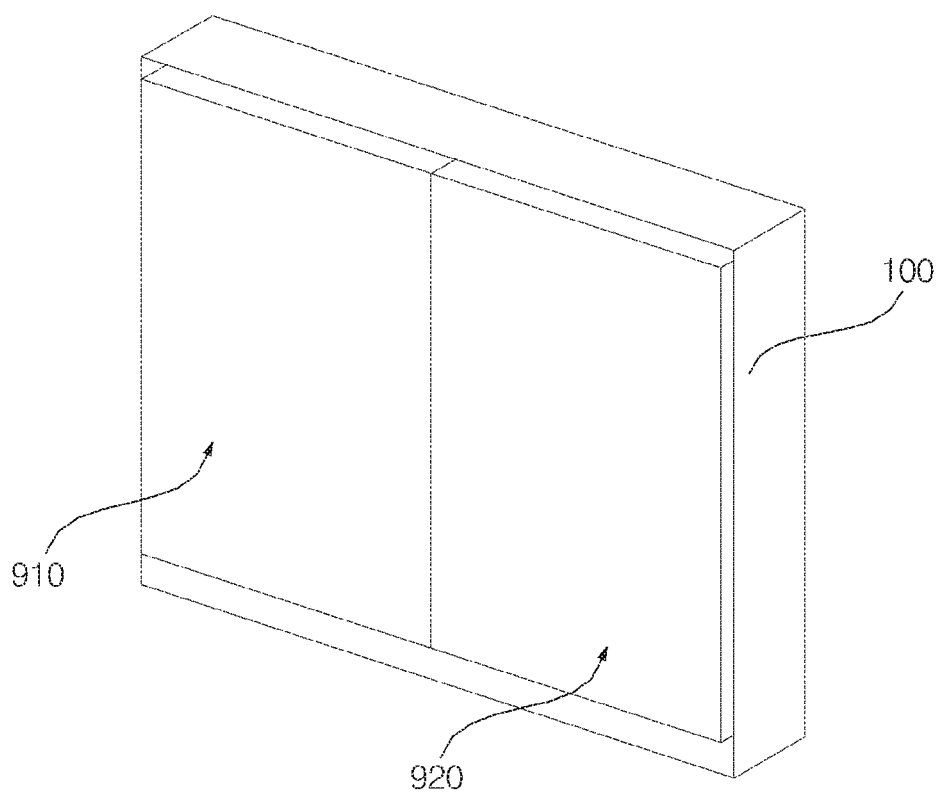
FIG. 1 is a perspective view showing a bathroom management apparatus according to an embodiment of the present disclosure.

Hereinafter, a bathroom management apparatus according to embodiments of the present disclosure will be described in detail with reference to the accompanying drawings.

In general, a bathroom is a place that allows users to wash his/her clothes, face, hands, shower, or the like. Since the bathroom is a very humid place, molds and bacteria may easily breed and may result in unwanted odors.

Most bathrooms dry and deodorize mainly relying on a ventilation fan. However, since an operation of the ventilation fan may not suitable or may be inadequate to dry the whole bathroom even with constant operation, the ventilation fan alone may be inadequate to control mold and the bacteria. Accordingly, it is important to prevent the bathroom from becoming a habitat of the molds and the bacteria by removing moisture early on, particularly at low lying areas of the bathroom, as well as promptly drying wet bath and toilet appliances such as wet towels.

Further, various facilities such as washstand, toilet, mirror, towel rack, toothbrush holder, as well as a storage space (or storage room) for storing various bath and toilet appliances including towels or the like, may be provided in the bathroom. Meanwhile, a user may use various types of electronic products such as hair dryers and shavers in the bathroom.

Hence, if a bathroom management apparatus can integrate multiple functions such as a toothbrush sterilizer, a cosmetics refrigerator, a charging function for electronic products, as well as drying or dehumidifying functions to address multiple needs in the bathroom, the space in the bathroom can be more effectively used.

Further, if a bath management apparatus can be customized to select only desired functions among various function modules including, for example, a storage module having a function for storage, an air conditioning module having a function to dry objects in the bathroom, a sterilizing module having a function of a toothbrush sterilizer, a refrigerating module having a function of a cosmetics refrigerator, and a charging module having a charging function for the electronic products, or the like, the effectiveness and usability of the bathroom management apparatus may be improved.

In addition, an installation position of the function modules may be freely changed by taking into consideration available storage space, convenience and usability to the user. Since a toilet, a washstand, and a mirror may each be installed in different locations in the bathroom, the installation position of the function module may be freely changed according to the applicable environment of the bathroom.

Meanwhile, a mirror may be installed at a door of a storage room installed in a bathroom may be used instead of a mirror in the bathroom. However, humidity and frost may be easily formed on the mirror due to humid air. In particular, when the user showers with hot water, humidity is easily formed due to frost from the hot water so that the mirror loses the function.

A first objective of the present disclosure provides a bathroom management apparatus capable of dehumidifying and defrosting a mirror installed at a door.

A second objective of the present disclosure provides a bathroom management apparatus capable of easily processing wiring of a light source or a heater installed in a door.

According to an aspect of the present disclosure, there is provided a bathroom management apparatus including: a cabinet of which a front surface is open; a door configured to open/close the open front surface of the cabinet and a mirror is provided at a front surface of the door, wherein the door comprises a heater disposed in a rearward direction of the mirror to heat the mirror.

The bathroom management apparatus as broadly described and embodied herein addresses these as well as other aspects.

Figure 2:
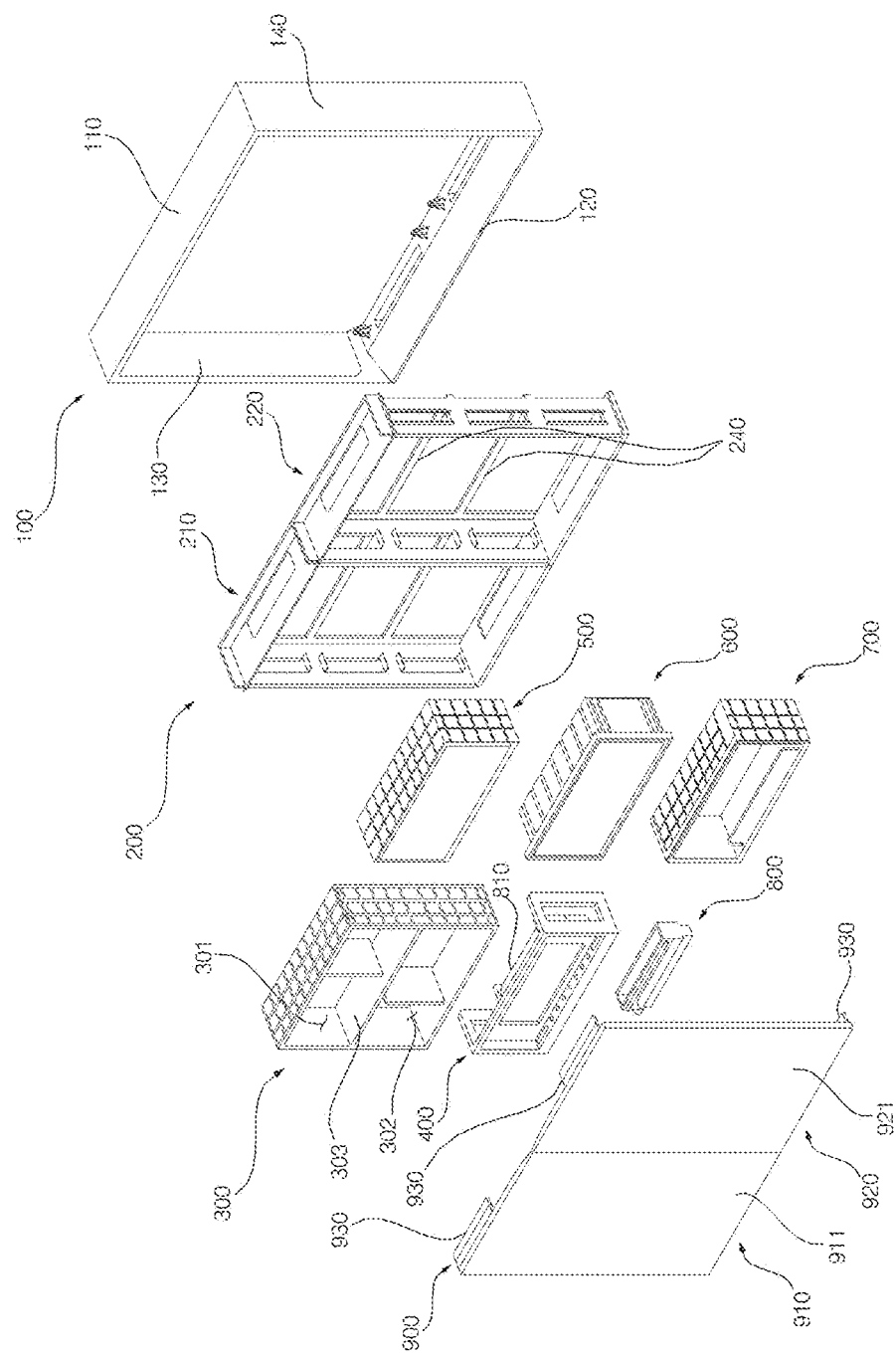
FIG. 2 is an exploded perspective view showing a bathroom management apparatus of FIG. 1.

FIG. 1 is a perspective view showing a bathroom management apparatus according to one embodiment of the present disclosure, and FIG. 2 is an exploded perspective view showing a bathroom management apparatus of FIG. 1. The bathroom management apparatus may include a cabinet 100, a frame 200 installed inside the cabinet 100, a plurality of function modules 300, 400, 500, 600, 700, and 800, and a door 900 disposed in a forward direction of the cabinet 100.

The cabinet 100 may have a hollow structure and may have a square shape of which a front surface and a rear surface are open. The cabinet 100 may form an upper external appearance, a lower external appearance, a left external appearance, and a right external appearance.

The cabinet 100 may include an upper panel 110 forming an upper side, a lower panel 120 forming a lower side, a left side panel 130 forming a left side, and a right side panel 140 forming a right side. The upper panel 110 connects a top end of the left side panel 130 with a top end of the right side panel 140. The lower panel 120 connects a bottom end of the left side panel 130 with a bottom end of the right side panel 140.

A left end of the upper panel 110 may be coupled with a top end of the left side panel 130 and a right end of the upper panel 110 may be coupled with a top end of the right side panel 130. Further, a left end of the lower panel 120 may be coupled with a lower end of the left side panel 130, and a right end of the lower panel 120 may be coupled with a bottom end of the right side panel 140.

The frame 200 may include frame bodies 210 and 220 having a square shape corresponding to the cabinet 100 of which a front surface and a rear surface are open, and back brackets 240 disposed in a rearward direction of the frame bodies 201 and 220 to be coupled with rear surfaces of the frame bodies 210 and 220. The frame bodies 210 and 220 reinforce stiffness of the cabinet 100. The bracket 240 may be thicker than the frame bodies 210 and 220 to reinforce the stiffness of the frame bodies 210 and 220.

The frame bodies 210 and 220 provide a space for multiple function modules 300, 400, 500, 600, 700, and 800. The function modules 300, 400, 500, 600, 700, and 800 include a towel care module 300 (or towel warmer), a sterilizing module 400 (or sterilizer), a secret box module 500 (or lock box), a refrigerating module 600 (or refrigerator), a charging module 700 (or device charger), and a blower out module 800 (or blower module, vane assembly). The towel care module 300, the sterilizing module 400, the secret box module 500, the refrigerating module 600, the charging module 700, and the blower module 800 may be independently provided and installed inside the frame bodies 210 and 220 as module units. Ribs protrude from upward, downward, left and right sides of the function modules 300, 400, 500, 600, 700, and 800, respectively. The ribs protrude from left and right sides of the function modules 300, 400, 500, 600, 700, and 800 may be supported by an inner rib 215 to be described later protruding in the frame bodies 210 and 220.

The towel care module 300 may be installed with a function division plate 303. The function division plate 303 divides an inner space of the towel care module 300. The towel care module 300 may include a first storage space 301 for storing towels at a top side of the function division plate 303 and a second storage space 302 for storing the towels at a bottom side of the function division plate 303, and configured to dry and warm the stored towels. The towel care module 300 may include a first independent towel care module having only the first storage space 301 without the function division plate 303 and a second independent towel care module having only the second storage space 302.

The sterilizing module 400 may be used as a toothbrush sterilizer. The sterilizing module 400 may be installed therein with toothbrushes, and may be installed therein with a lamp for irradiating ultra violet ray to the toothbrushes. A blower module 800 may be installed at a bottom side of the sterilizing module 400. An air conditioning module 810 (or dryer) including a blower for sucking and blowing air to the blower module 800 and a heater for heating the air blown from the blower is installed at a rearward direction of the sterilizing module 400 corresponding to a top side of the blower module 800 so that the sterilizing module 400 and the air conditioning module 810 may be integrally formed. The blower module 800 may exhaust the air blown from the blower into an inside of the bathroom.

The secret box module 500 may be used as storage for storing objects to prohibit children and customers to see or touch. The secret box module 500 may be a lock box, or the like, and may be secured.

The refrigerating module 600 may be used as usage for refrigerating medicines and cosmetics. The refrigerating module 600 may be installed with a thermoelectric module for supplying cold air into the refrigerating module 600 and for emitting warm air to an outside of the refrigerating module 600.

The charging module 700 may be used as usage for charging electronic devices such as a hair dryer and an electric shaver. The charging module 700 may be installed therein with a holder for holding the hair dryer and with a receptacle in which a power plug of the electronic device or a power plug of a charger for charging the electronic device.

Two frame bodies 210 and 220 may be provided and include a first frame body 210 and a second frame body 220 disposed at one side of the first frame body 210. The first frame body 210 and the second frame body 220 have the same structure. The desired modules may be customized based on user need. For example, desired ones among the towel care module 300, the sterilizing module 400, the secret box module 500, the refrigerating module 600, the charging module 700, and the blower module 800 may be selected and installed according to a need of a consumer. For example, only a plurality of towel care modules 300 may be installed, or alternatively, two towel care modules 300 and one refrigerating module 600 may be installed in the frame bodies 210 and 220. According to the number of towel care modules 300, the sterilizing modules 400, the secret box modules 500, the refrigerating modules 600, and the charging modules 700 installed in the frame bodies 210 and 220, one or more frame bodies 210 and 220 may be provided.

The door 900 may form a front external appearance of the bathroom management apparatus. The door 900 opens/closes an open front surface of the cabinet 100. The same number of doors 900 is provided by the corresponding number of the frame bodies 210 and 220. Since the two frame bodies 210 and 220 are provided, two doors 900 are provided to include a first door 910 and a second door 920. The first door 910 may be disposed in a forward direction of the first frame body 210 and opens a left side of an open front surface of the cabinet 100, and the second door 920 may be disposed in a forward direction of the second frame body 220 and opens a right side of an open front surface of the cabinet 100.

Mirrors 911 and 912 may be provided at front surfaces of the first door 910 and the second door 920, respectively. The mirrors 911 and 921 may be used instead of a mirror inside the bathroom. The mirrors 911 and 921 include a first mirror 911 provided at a front surface of the first door 910 and a second mirror 921 provided at a front surface of the second door 920.

A hinge 930 may be installed at a rear surface of the door 900. The hinge 930 may include a first hinge member of which one end is coupled with a rear surface of the door and a second hinge member of which one end is rotatably coupled with an opposite end of the first hinge member and an opposite end is rotatably coupled with the frame bodies 210 and 220. The hinges 930 may be installed at a top side and a lower side of a rear surface of the first door 910, respectively, and may be installed at a top side and a bottom side of a rear side of the second door 910.

Figure 3:
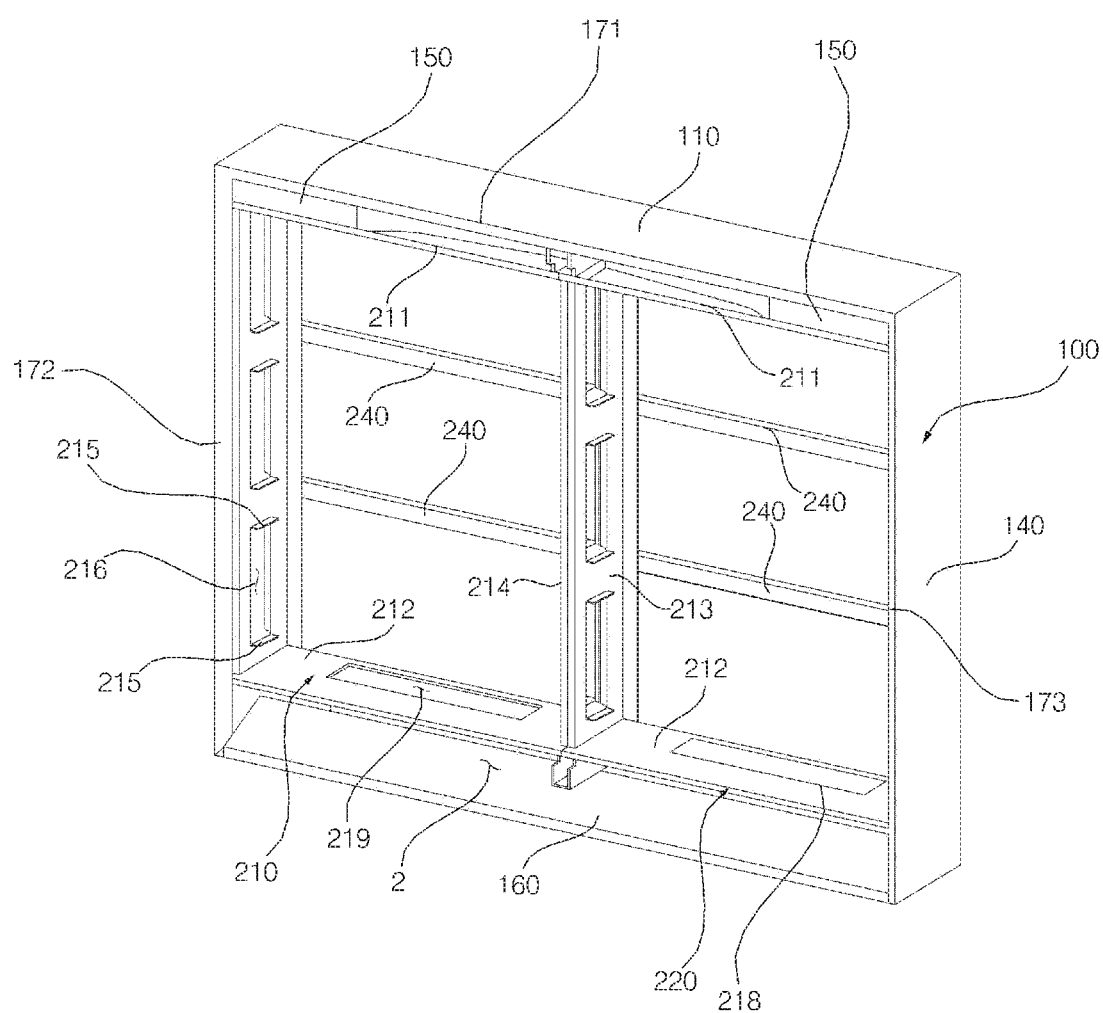
FIG. 3 is a view illustrating a coupled state between the cabinet and the frame.
Figure 4:
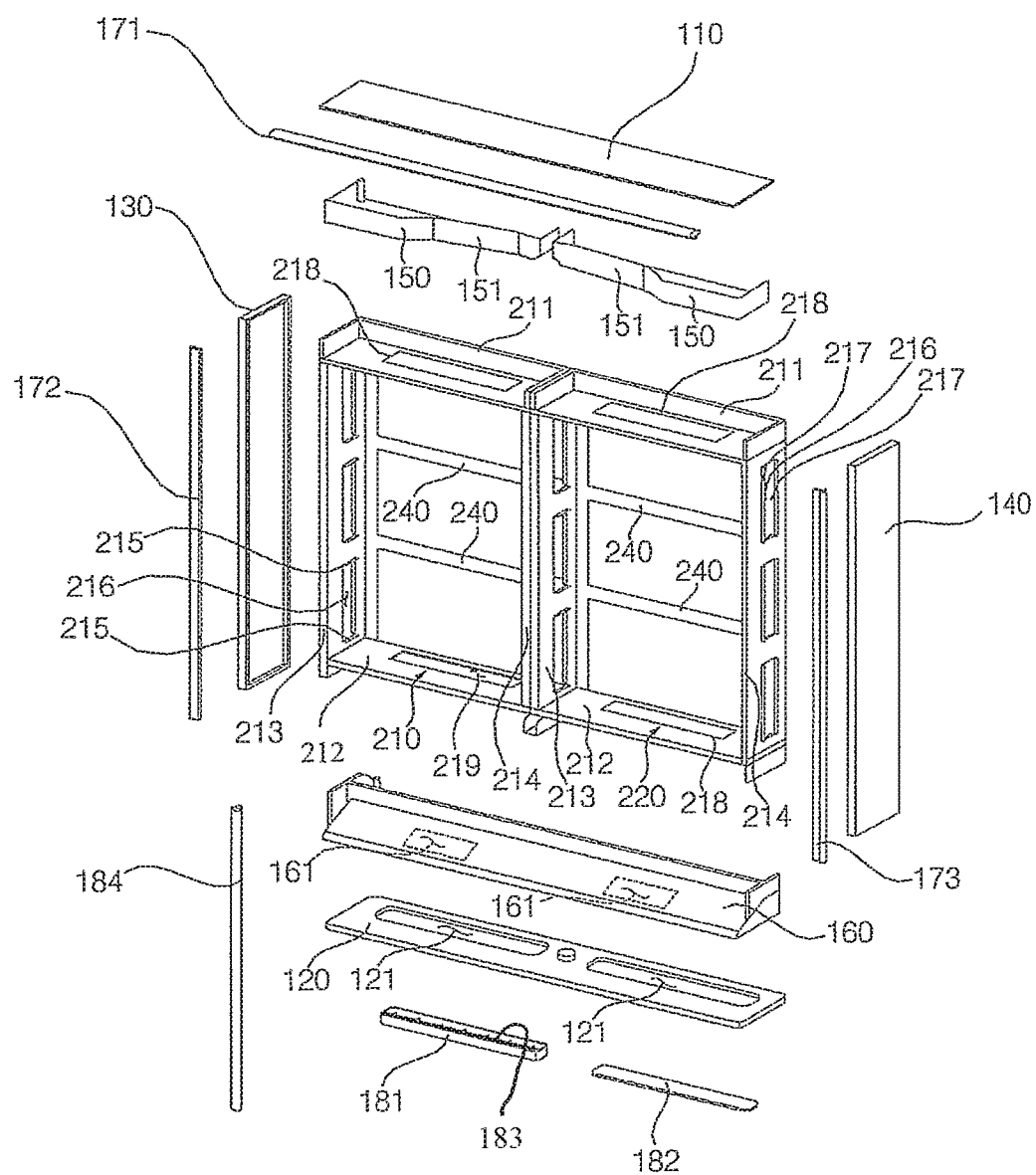
FIG. 4 is an exploded perspective view of FIG. 3.

FIG. 3 is a view illustrating a coupled state between the cabinet and the frame shown in FIG. 3, and FIG. 4 is an exploded perspective view of FIG. 3. Top surfaces and bottom surfaces of frame bodies 210 and 220 may be spaced apart from the cabinet 100. That is, the top surfaces of the frame bodies 210 and 220 may be vertically spaced apart from the upper panel 110 of the cabinet 100, and the bottom surfaces of the frame bodies 210 and 220 may be vertically spaced apart from the lower panel 110 of the cabinet 100.

An upper cover 150 may be disposed at a space between the upper panel 110 of the cabinet 100 and the top surfaces of the frame bodies 210 and 220. The upper cover 150 may be inserted into the space between the upper panel 110 of the cabinet 100 and the top surfaces of the frame bodies 210 and 220 to be coupled with the upper panel 110 of the cabinet 100 and the top surfaces of the frame bodies 210 and 220.

When a door 900 is closed, the upper cover 150 covers the space between the upper panel 110 of the cabinet 100 and the top surfaces of the frame bodies 210 and 220, a hinge 930 installed at a rear top side of the door 900 is not viewable from a rear direction of the bathroom management apparatus through a space between the upper panel 110 and top surfaces of the frame bodies 210 and 220. When the door 900 is open, the upper cover 150 prevents the bathroom wall from being viewed from the forward direction of the bathroom management apparatus through a space between the upper panel 110 and the top surface of the frame bodies 210 and 220. The upper cover 150 may have a shape in which a top surface and a rear surface are open to include a bottom surface, a front surface, a left surface, and a right surface.

A concave groove 151 for receiving a hinge 930 when the door 900 is closed is formed at the front surface of the upper cover 150 so that a space for receiving the hinge 930 may be formed between the upper panel 110 and the top surfaces of the frame bodies 210 and 220.

Further, a control panel 160 may be inserted between the lower panel 120 of the cabinet 100 and bottom surfaces of the frame bodies 210 and 220. The control panel 160 may be inserted between the lower panel 120 of the cabinet 100 and bottom surfaces of the frame bodies 210 and 220 to be coupled with the lower panel 120 of the cabinet 100 and the bottom surfaces of the frame bodies 210 and 220.

Remaining regions of the control panel 160 except for a top side coupled with the bottom surfaces of the frame bodies 210 and 220 may be spaced apart from the bottom surfaces of the frame bodies 210 and 220. Air exhausted from the blower module 800 may be moved into a first air outlet 2 through a space between bottom surfaces of the frame bodies 210 and 220 and a top side of the control panel 160. Hence, after a shower, the user may dry off using air exhausted through the first air outlet 2.

A user interface as well as an input unit for controlling function modules 300, 400, 500, 600, 700, 800, and 810 may be installed at the control panel 160. The input unit may include at least one of a button and a touch screen, and the user pushes or touches the input unit to operate or stop the function modules 300, 400, 500, 600, 700, 800, and 810. An installed region of the input unit of the control panel 160 may be exposed below the door 900 when the door 900 is closed.

Meanwhile, the cabinet 100 may include decoration members 171, 172, and 173 coupled with a front end of the upper panel 110, a front end of the left side panel 130, and a front end of the right side panel 140, respectively. The decoration members 171, 172, and 173 include a first decoration member 171 coupled with a front end of the upper panel 100, a second decoration member 172 coupled with a front end of the left side panel 130, and a third decoration member 173 coupled with a front end of the right side panel 140. The decoration members 171, 172, and 173 are not installed at a front end of the lower panel 120. Instead, the front end of the lower panel 120 may be covered by a front end of the control panel 160. That is, the control panel 160 may function as a decoration members by covering the front end of the lower panel 120. The control panel 160 may be formed with the same color and material as those of the decoration members 171, 172, and 173. The frame bodies 210 and 220 may include an upper frame 211 forming an upper side, a lower frame 212 forming a lower side, and a left side frame 213 forming a left side, and a right side frame 214 forming a right side.

The upper frame 211 connects a top end of the left side frame 213 with a top end of the right side frame 214. The lower frame 212 connects a bottom end of the left side frame 213 with a bottom end of the right side frame 214.

A left end of the upper frame 211 may be coupled with a top end of the left side frame 213, and a right end of the upper frame 211 may be coupled with a top end of the right side frame 214. Further, a left end of the lower frame 212 may be coupled with a bottom end of the left side frame 213, and a right end of the lower frame 212 may be coupled with a bottom end of the right side frame 214.

The upper frame 211 and the lower frame 212 may have the same structure. The left side frame 213 and the right side frame 214 may have the same structure. Accordingly, the frame body 210 and the second frame body 220 may be installed inside the cabinet 100 regardless of upper and lower sides and regardless of left and right sides.

The upper frame 211 may have a shape in which a top surface and a front surface are open and may include a bottom surface, a left surface, a right surface, and a rear surface. Further, the lower frame 212 has a shape that is upside down relative to the upper frame 211 and may include a bottom surface and a front surface which are open. That is, the lower frame 212 may include a left surface, a right surface, and a rear surface.

First opening portions 216 having a square shape may be formed in the left side frame 213 and the right side frame 214, respectively. The first opening portion 216 may form a path through which wires of the function modules 300, 400, 500, 600, 700, and 800 may pass. A same number of first opening portions 216 may be formed corresponding to the number of function modules 300, 400, 500, 600, 700, and 800 installed inside the frame bodies 210 and 220.

Inner ribs 215 may be formed at inner sides of the left side frame 213 and the right side frame 214, respectively. The inner ribs 215 protrudes inward from the frame bodies 210 and 220 at a top side and a bottom side of the first opening portion 216.

The inner rib 215 may guide insertion of the function modules 300, 400, 500, 600, 700, and 800 when the function modules 300, 400, 500, 600, 700, and 800 are individually inserted into the frame bodies 210 and 220. After the function modules 300, 400, 500, 600, 700, and 800 are inserted into the frame bodies 210 and 220, the inner rib 215 may support the function modules 300, 400, 500, 600, 700, and 800.

Outer ribs 217 may be formed at outer sides of the left side frame 213 and the right side frame 214, respectively. The outer ribs 217 may protrude to outer sides of the frame bodies 210 and 220 from a front side and a rear side of the first opening portion 216, respectively.

The outer ribs 217 may be spaced a part from each other in forward and reward directions while interposing the first opening portion 216 therebetween to form a path through which wires of the function modules 300, 400, 500, 600, 700, and 800 pass after the wires of the function modules 300, 400, 500, 600, 700, and 800 pass through the first opening portion 216.

Cut lines 218 having a square shape are formed at a bottom surface of the upper frame 211 and a top surface of the lower frame 212, respectively. The cut lines 218 may be formed by partially cutting a bottom surface of the upper frame 211 and a top surface of the lower frame 212 so that a worker may easily separate an inner region divided by the cut lines 218 from a bottom surface of the upper frame 211 an a top surface of the lower frame 212.

When the sterilizing module 400 is installed close to the upper frame, a worker may cut the cut line 218 formed at the upper frame 211 among the cut line 218 formed at the upper frame 211 and the cut line 218 formed at the lower frame 212 to separate an inner region of the upper frame 211 divided by the cut line 218. When the sterilizing module 400 is installed close to the lower frame, the worker may cut the cut line 218 formed at the lower frame 211 among the cut line 218 formed at the upper frame 211 and the cut line 218 formed at the lower frame 212 to separate an inner region of the lower frame 212 divided by the cut line 218.

The second opening portions 219 may be formed at the upper frame 211 and the lower frame 212 when the inner region divided by the cut line 218 is separated by the worker. Further, a third opening portion 161 may be formed at a lower side of the second opening portion 219 in a lower side of the control panel 160. Further, a fourth opening portion 121 may be formed at a lower side of the third opening portion 161 in a lower panel 120 of the cabinet 100.

A blower louver 181 or a lower cover 182 may be provided at the fourth opening portion 121. The blower louver 181 may be installed at a region corresponding to the fourth opening portion 121 or a lower cover 182 may be installed on the top surface of the lower panel 120. When the fourth opening portion 121 is located under the sterilizing module 400, for example, the blower louver 181 may be installed at a region corresponding to the fourth opening portion 121 in the lower panel 120. Otherwise, a lower cover 182 may be installed at a region corresponding to the fourth opening portion 121 in the lower panel 120 so that the fourth opening portion 121 is shielded by the lower cover 182.

The blower louver 181 may include a discharge grill 183, and may be installed at a region corresponding to the fourth opening portion 121 in the lower panel 120 to guide air from the blower module 800 into the fourth opening portion 121. When the blower louver 182 is installed at a region corresponding to the fourth opening portion 121 in the lower panel 120, the fourth opening portion 121 becomes the second air outlet 121. That is, in the cabinet 100, the first air outlet 2 is spaced apart from a lower frame 212 being a bottom surface of the frame 200, and a second air outlet 121 may be formed at a bottom surface of the frame 200.

The blower module 800 may be disposed inside the control panel 160 between the lower panel 120 and the lower frame 212. Further, a top end of the blower module 800 may be inserted into the second opening portion 219 so that air blown from the blower flows though the blower module 800, and a bottom end of the blower module 800 is connected to the blower louver 181 through the third opening portion 161. Moreover, a front opening portion communicating with the first air outlet 2 may be formed at a front surface of the blower module 800.

Since the blower module 800 may be installed with a motor and a fluid path switching vane rotated by a driving force of the motor, the fluid path switching vane is rotated by the driving force of the motor to open the front opening portion and close a bottom end, such that air flowing from an air conditioning module 810 passes through the front opening portion and is discharged into the bathroom through the first air outlet 2. When the front opening portion is closed and the bottom end is open, the air flowing from the blower passes through the blower louver 181 and is discharged into the bathroom through the second air outlet 121. That is, the blower module 800 switches the direction of air blown from the air conditioning module 810 to one of the first air outlet 2 and the second air outlet 121.

A user may control a rotation position of the fluid path switching vane of the blower module 800 by operating the input unit installed at the control panel 160 to discharge air into the bathroom through the first air outlet 2 or to discharge the air into the bathroom through the second air outlet 121. The air discharged into the bathroom through the first air outlet 2 may be used to dry the user's body. The air discharged into the bathroom through the second air outlet 121 may be used to dry an inside of the bathroom.

Meanwhile, when a plurality of frame bodies 210 and 220 are provided, a center cover 184 may be further installed at front surfaces of adjacent side frames 214 and 213 of the plurality of frame bodies 210 and 220. That is, in the present embodiment, two frame bodies 210 and 220 are provided, center covers 184 may be installed at a front surface of the right side frame 214 of the first frame body 210 and a front surface of a left side frame 213 of the second frame body 220, respectively. The center cover 184 may cover the right side frame 214 of the first frame body 210 and the left side frame 213 of the second frame body 220 in a forward direction. In addition, after the function modules 300, 400, 500, 600, and 700 are inserted into the frame bodies 210 and 220, the center cover 184 may protrude to both sides of the function modules 300, 400, 500, 600, and 700 to cover a module locking rib which is locked at a front surface of the both side frames 213 and 214 of the frame bodies 210 and 220.

Hereinafter, a structure of a door 900 will be described with reference to FIG. 5 to FIG. 9. However, since the first door 910 and a second door 920 have the same structure, only a first door 910 is described as an example of a door 900, and a first mirror 911 provided at a front surface of the first door 910 is described as a mirror 911.

Figure 5:
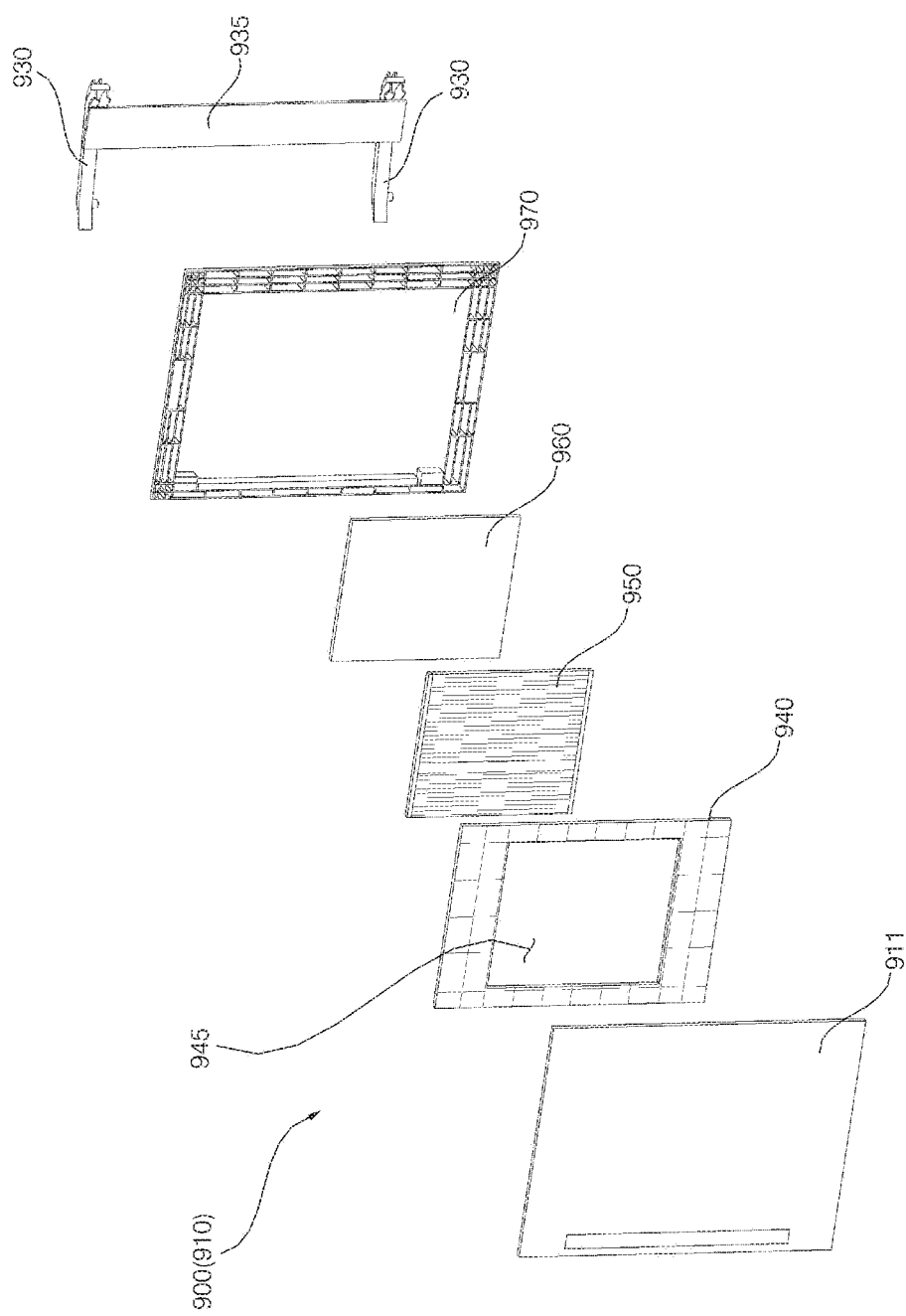
FIG. 5 is an exploded perspective view illustrating a door shown in FIG. 1 and FIG. 2.

FIG. 5 is an exploded perspective view illustrating a door shown in FIG. 1 and FIG. 2.

Referring to FIG. 5, a door 900 includes a mirror 911 forming a front surface, an outer frame 970 forming a rear surface, an inner frame 940, a heater 950, and an insulation plate 960 disposed between the mirror 911 and the outer frame 970.

Since the door 900 has a square shape, all of the mirror 911, the outer frame 970, the inner frame 940, the heater 950, and the insulation plate 960 have a square shape.

The mirror 911 and the outer frame 970 have the same size to form an outer appearance of the door 900. Further, the inner frame 940, the heater 950, and the insulation plate 960 have a size smaller than that of the mirror 911 and the outer frame 970 and are disposed at an inside between the mirror 911 and the outer frame 970.

The inner frame 940 is disposed in a rearward direction (or rear, behind) of the mirror 911. The heater 950 is disposed in a rear direction of the inner frame 940. The insulation plate 960 is disposed in a rearward direction of the heater 950. The outer frame 970 is disposed in a rear direction of the insulation plate 960. The inner frame 940 is disposed between the mirror 911 and the heater 950. The heater 950 is disposed between the inner frame 940 and the insulation plate 960. The insulation plate 960 is disposed between the heater 950 and the outer frame 970. The mirror 911 may be coupled with a front surface of the inner frame 940 to be provided at a front surface of the outer frame 970. The mirror 911 may adhere to a front surface of the inner frame 940 by adhesive.

A rear surface of the inner frame 940 is coupled with an outer frame 970 in a state that a mirror 911 is coupled with a front surface of the inner frame 940. The inner frame 940 is formed therein with an opening hole 945 (or opening) communicating with the heater 950. The opening hole 945 may be the size and the shape corresponding to a heat generating part to have a square shape.

The heater 950 includes a surface electric heater for converting electric energy into heat energy. Heat generated from the heater 950 is transferred to a mirror 911 through an opening hole 945 of the inner frame 940 to heat the mirror 911. Accordingly, humidity or frost formed on a front surface of the mirror 911 may be removed by heat generated from the heater 950. The heater 950 has a size smaller than that of the inner frame 940.

The heater 950 may be disposed adjacent to the inner frame 940. The heater 950 is positioned behind the inner frame 940 such that a prescribed gap is provided between the heater 950 and the inner frame 940. Heat may be transferred to the mirror 911 through the opening 945. Alternatively, the heater 950 may be provided in the opening 945 and may contact the rear of the mirror 911.

The insulation plate 960 prevents heat generated from the heater 950 from being leaked to a reward direction of the heater 950 to improve dehumidification and defrost efficiency. The insulation plate 960 has the same shape as that of the heater 950.

A hinge 930 may be coupled with a rear surface of the outer frame 970. Two hinges 930 are connected to each other by a connection member 935. Hinges 930 may be coupled with a top end and a bottom end of the connection member 935, respectively. A hinge 930 coupled with a top end of the connection member 935 is coupled with an upper rear side of the outer frame 970. A hinge coupled with a bottom end of the connection member 935 is coupled with a lower rear side of the outer frame 970.

FIG. 6 is a view illustrating a process of coupling an inner frame and an outer frame shown in FIG. 5.

Referring to FIG. 5 and FIG. 6, a front surface of the outer frame 970 includes an inner frame mounting part 978 (or inner frame mounting region or surface) on which an inner frame 940 is mounted and a stiffness reinforcing part 979 (or stiffness reinforcing region or surface) disposed at an outer edge of the inner frame mounting part 978. The inner frame mounting part 978 has the same shape as that of the inner frame 940 to have a square shape. The stiffness reinforcing parts 979 are disposed at outer sides of the inner frame mounting part 978, respectively.

Although FIG. 6 illustrates an insulation plate 960 and a heater 950, substantially, after the insulation plate 960 and the heater 950 are mounted on an inner frame mounting part 978, the inner frame 940 is mounted on the inner frame mounting part 978.

Figure 7:
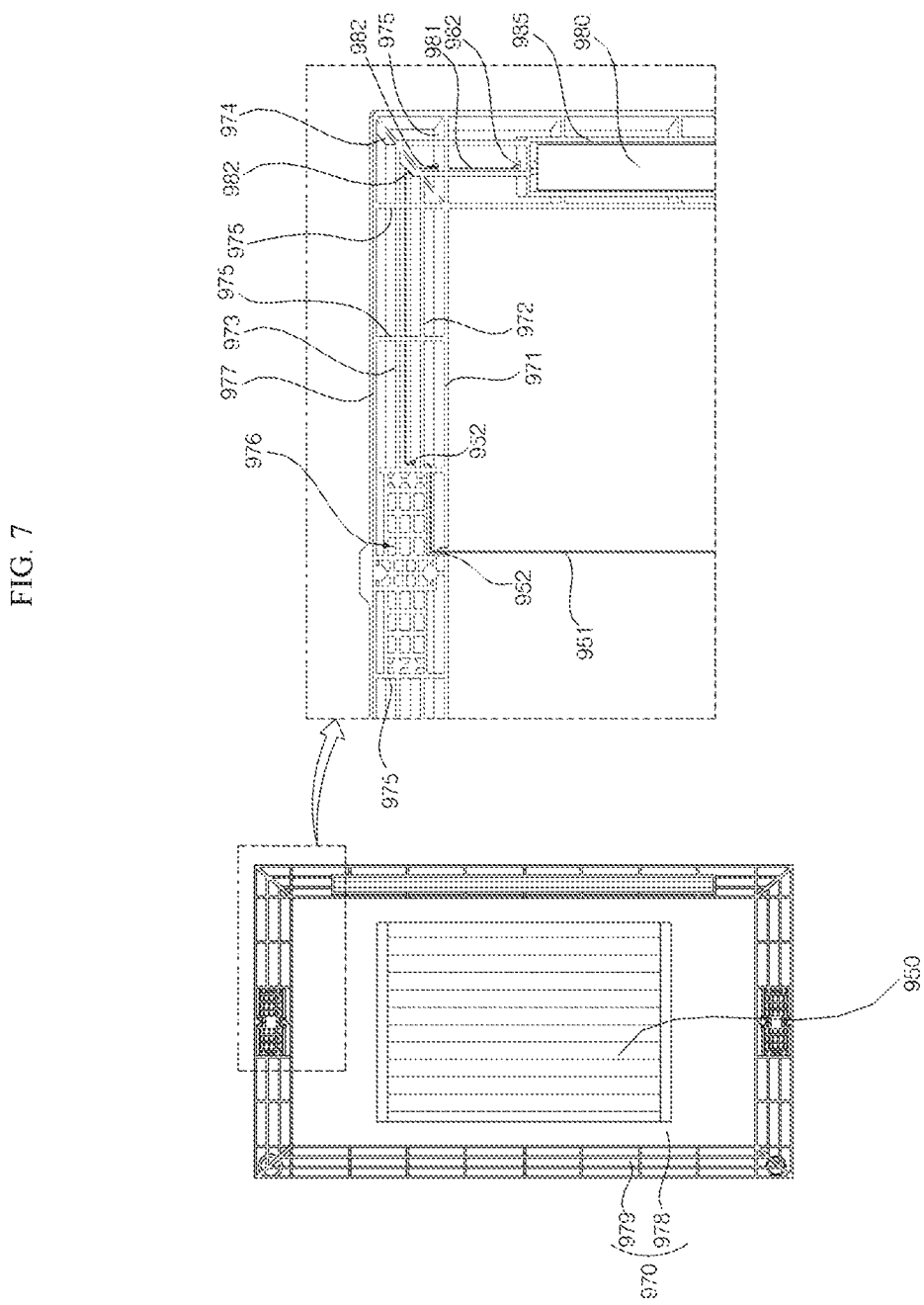
FIG. 7 illustrates a front surface of an outer frame shown in FIG. 6.

FIG. 7 illustrates a front surface of an outer frame shown in FIG. 6.

Stiffness reinforcing ribs 971, 972, 973, 974, 975, and 976 are formed at a stiffness reinforcing part 979 of the outer frame 970.

The stiffness reinforcing ribs 971, 972, 973, 974, 975, and 976 may include a first stiffness reinforcing rib 971, a second stiffness reinforcing rib 972, a third stiffness reinforcing rib 973, a fourth stiffness reinforcing rib 974, a fifth stiffness reinforcing rib 975, and a sixth stiffness reinforcing rib 976. The first stiffness reinforcing rib 971 may have a square shape to surround an edge of the inner frame 940.

The second stiffness reinforcing rib 972 may be spaced apart from the first stiffness reinforcing rib 971 to surround the first stiffness reinforcing rib 971. The third stiffness reinforcing rib 973 is spaced apart from the second stiffness reinforcing rib 972 to surround the second stiffness reinforcing rib 972. The second stiffness reinforcing rib 972 and the third stiffness reinforcing rib 973 have a square shape and have a shape of which a horizontal center of a top end and a horizontal center of a bottom end are cut.

The fourth stiffness reinforcing rib 974 connects an edge of the first stiffness reinforcing rib 971, an edge of the second stiffness reinforcing rib 972, and an edge of the third stiffness reinforcing rib 971 with an edge of an outer periphery 977 (or outer peripheral rib) of the stiffness reinforcing part 979. A plurality of fourth stiffness reinforcing ribs 974 is provided. That is, the plurality of fourth stiffness reinforcing ribs 974 connects four edges of the first stiffness reinforcing rib 971, four edges of the second stiffness reinforcing rib 972, and four edges of the third stiffness reinforcing rib 971 with four edges of an outer periphery 977 of the stiffness reinforcing part 979, respectively so that total four fourth stiffness reinforcing ribs 974 are formed.

The fifth stiffness reinforcing rib 975 connects a region except for the edge of the first stiffness reinforcing rib 971, a region except for the edge of the second stiffness reinforcing rib 972, and a region except for the edge of the third stiffness reinforcing rib 973 with a region except for the edge of an outer periphery 977 of the stiffness reinforcing part 979.

A plurality of fifth stiffness reinforcing ribs 975 may be provided. The plurality of fifth stiffness reinforcing ribs 975 are connected to four sides of the first stiffness reinforcing rib 971, respectively. Some of the plurality of fifth stiffness reinforcing ribs 975 are disposed at right and left ends of open top sides and bottom sides of the second stiffness reinforcing rib 972 and the third stiffness reinforcing rib 973.

A plurality of sixth stiffness reinforcing ribs 976 may be provided. In the plurality of sixth stiffness reinforcing ribs 976, total two sixth stiffness reinforcing ribs 976 may be provided where one sixth stiffness reinforcing rib 976 is provided at a horizontal center of a top side of the first stiffness reinforcing rib 971 and the other six stiffness reinforcing rib 976 is provided at a horizontal center of a bottom side of the first stiffness reinforcing rib 971. A horizontal center of a top side and a bottom side of the first stiffness reinforcing rib 971 corresponds to a coupling region of the hinge 930 in the rear surface of the outer frame 970. Since the whole load of the door 900 is supported by the hinge 930, a horizontal center of a top side and a bottom side of the first stiffness reinforcing rib 971 requires higher stiffness than remaining regions. Accordingly, it is preferred that the six stiffness reinforcing rib 976 has a lattice shape to have stiffness higher than that of the first stiffness reinforcing rib 971, the second stiffness reinforcing rib 972, the third stiffness reinforcing rib 973, the fourth stiffness reinforcing rib 974, and the fifth stiffness reinforcing rib 975. A plurality of six stiffness reinforcing ribs 976 are connected with the fifth stiffness reinforcing ribs 975 of the plurality of the fifth stiffness reinforcing ribs 975 disposed at right and left ends of the open top side and the open bottom side of the second stiffness reinforcing rib 972 and the third stiffness reinforcing rib 973, and with the first stiffness reinforcing rib 971, and an outer peripheral portion 977 of the stiffness reinforcing part 979.

The plurality of first stiffness reinforcing ribs may be disposed concentrically relative to the plurality of second stiffness reinforcing ribs and the plurality of third stiffness reinforcing ribs as illustrated in FIG. 7. The second stiffness reinforcing ribs may be provided at a prescribed distance away from the first stiffness reinforcing ribs and the third stiffness reinforcing ribs. The plurality of stiffness reinforcing ribs may be formed to have a same height relative to the front surface of the outer frame. This may provide a secure connection of the outer frame 970 to the mirror 911. The heights may also be different. As shown, a plurality of recesses may be formed by the arrangement of the plurality of stiffness reinforcing ribs.

The door 900 may be further provided therein with a light source 980. The light source 980 creates and irradiates light to a mirror 911 to softly emit one side of the mirror 911. The light source 980 includes a light emitting diode (LED). A light source mounting part 985 is formed at the stiffness reinforcing part 979 of the outer frame 970 so that the light source 980 is inserted and mounted in one of the light source mounting part 985.

The light source mounting part 985 may be disposed at a center point of the stiffness reinforcing part 979 and may be connected with the second stiffness reinforcing rib 972, the third stiffness reinforcing rib 973, and a plurality of fifth stiffness reinforcing ribs 975. The light source mounting part 985 may be provided at a lateral center region on the upper part and the lower part of the outer frame 970 as shown in FIG. 7.

First wiring holes 982 through which electric wires of the light source 980 pass may be formed in at least one of the first stiffness reinforcing rib 971, the second stiffness reinforcing rib 972, the third stiffness reinforcing rib 973, the fourth stiffness reinforcing rib 974, the fifth stiffness reinforcing rib 975, and the sixth stiffness reinforcing rib 976 and the light source mounting part 985, respectively. In the present embodiment, the first wiring holes 982 are formed at a top surface of the light source mounting part 985, the fourth stiffness reinforcing rib 974 and the fifth stiffness reinforcing rib 975 located at a top side of the light source mounting part 985, two fifth stiffness reinforcing ribs 975 located at a left side of the fourth stiffness reinforcing rib 974 located at a top side of the light source mounting part 985, the second stiffness reinforcing rib 972 located at a right side of the sixth stiffness reinforcing rib 976, and the fifth stiffness reinforcing rib 975 disposed at a right end of open top sides of the second stiffness reinforcing rib 972 and the third stiffness reinforcing rib 973, respectively.

Further, second wiring holes 952 through which electric wires 951 of the light source 980 pass may be formed in at least one of the first stiffness reinforcing rib 971, the second stiffness reinforcing rib 972, the third stiffness reinforcing rib 973, the fourth stiffness reinforcing rib 974, the fifth stiffness reinforcing rib 975, and the sixth stiffness reinforcing rib 976, respectively. In the present embodiment, the second wiring holes 952 are formed at the first stiffness reinforcing rib 971

The electric wires 981 of the light source 980 passing through the first wiring holes 982 and the electric wires 951 of the light source 980 passing through the second wiring holes 952 are separated from a rear surface of the outer frame 970 around the sixth stiffness reinforcing rib 976 to be covered by the hinge 930. It is preferred that holes are formed through which the electric wires 981 of the light source 980 and the electric wires 951 of the light source 980 separated from a rear surface of the outer frame 970. The electric wires 981 of the light source 980 and the electric wires 951 of the light source 980 separated from a rear surface of the outer frame 970 are configured along a length of the hinge 930.

Figure 8:
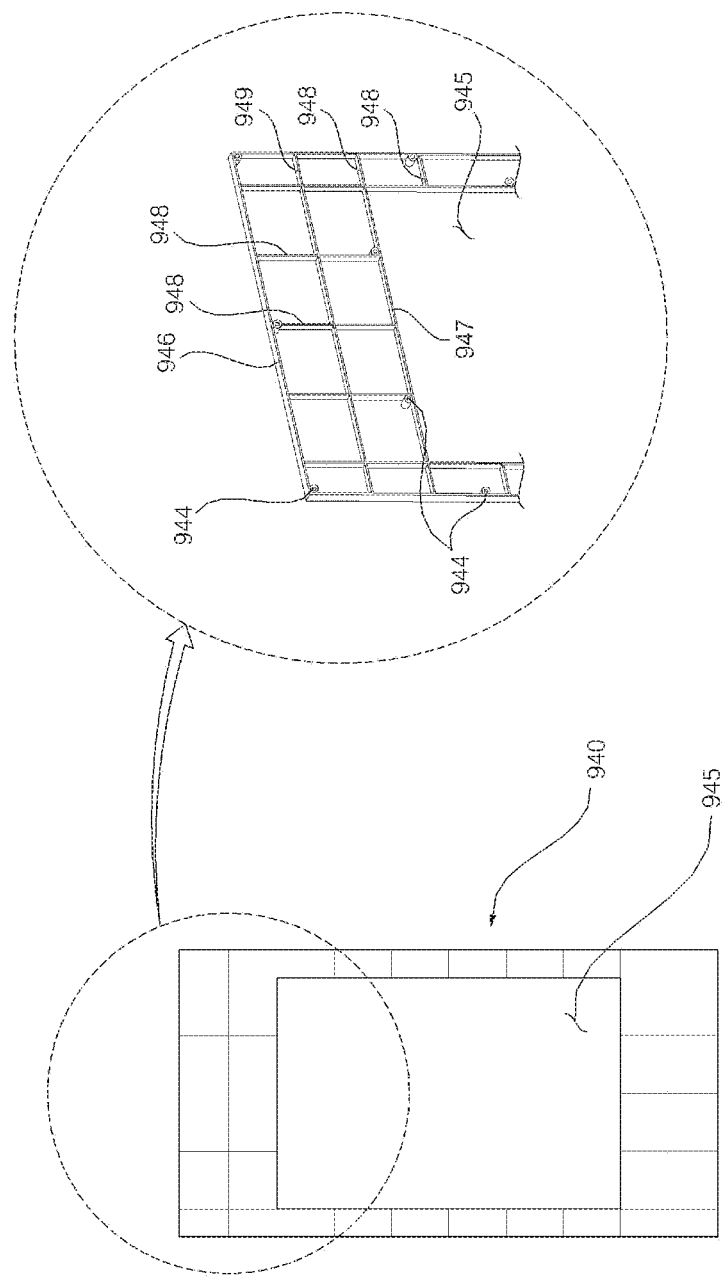
FIG. 8 is a view illustrating a rear surface of an inner frame shown in FIG. 6.

FIG. 8 is a view illustrating a rear surface of an inner frame shown in FIG. 6. The stiffness reinforcing ribs 947, 948, and 949 are formed at a rear surface of the inner frame 940. The stiffness reinforcing ribs 947, 948, and 949 include a seventh stiffness reinforcing rib 947, an eighth stiffness reinforcing rib 948, and a ninth stiffness reinforcing rib 949. The seventh stiffness reinforcing rib 947 may have a square shape surrounding an opening hole 945. The eighth stiffness reinforcing rib 948 is connected to the seventh stiffness reinforcing rib 947 and an outer peripheral portion 946 of the inner frame 940. A plurality of eighth stiffness reinforcing ribs 948 is provided. The plurality of eighth stiffness reinforcing ribs 948 are connected to four sides of the seventh stiffness reinforcing rib 947.

A plurality of ninth stiffness reinforcing ribs 949 is provided. The plurality of ninth stiffness reinforcing ribs 949 are spaced apart from a top side and a bottom side of the seventh stiffness reinforcing rib 947. The plurality of ninth stiffness reinforcing ribs 949 are connected to the plurality of eighth stiffness reinforcing ribs 948 and an outer peripheral portion of the inner frame 940. FIG. 9 is a view illustrating a hinge and an outer frame shown in FIG. 5. An inner frame boss 944 may be formed at a rear surface of the inner frame 940, and the outer frame 970 is formed therein with an inner frame locking hole 984 locking with the inner frame boss 944 through a screw. A plurality of inner frame bosses 944 and a plurality of inner frame locking holes 984 may be provided. A plurality of inner frame bosses 944 and a plurality of inner frame locking holes 984 are provided in one-to-one correspondence. The screw is inserted into the inner frame locking hole 984 at a rear surface of the outer frame 970 to be locked with the inner frame boss 944 so that the inner frame 940 is coupled with the outer frame 970.

Meanwhile, the outer frame 970 may be formed therein with a hinge locking hole 983 locked with the hinge 930. Since the hinges 930 may be coupled with a rear top portion and a rear bottom portion of the outer frame 970, it is preferred that the hinge locking holes 983 are formed at a top portion and a bottom portion of the outer frame 970, respectively. Further, the locking hole 933 may be formed at the hinge 930 so that the screw is sequentially inserted and locked in the locking hole 933 and the hinge locking hole 983 so that the hinge 930 is coupled with the outer frame 970.

As described above, in the bathroom management apparatus, a mirror 911 provided at a front surface of a door 900 may be dehumidified and defrosted by heat generated from a heater 950 provided in the door 900.

In addition, wiring of a light source 980 installed in the door 900 is easily processed through first wiring holes 982 formed in stiffness reinforcing ribs 971, 972, 973, 974, 975, 976 and a light source mounting part 985, and wiring of a heater 950 is easily processed through a second wiring hole 952 formed in the stiffness reinforcing ribs 971, 972, 973, 974, 975, 976.

A bathroom management apparatus is broadly described and embodied herein. A first objective of the present disclosure provides a bathroom management apparatus capable of dehumidifying and defrosting a mirror installed at a door.

A second objective of the present disclosure provides a bathroom management apparatus capable of easily processing wiring of a light source or a heater installed in a door.

According to an aspect of the present disclosure, there is provided a bathroom management apparatus including: a cabinet of which a front surface is open; a door configured to open/close the open front surface of the cabinet and a mirror is provided at a front surface of the door, wherein the door comprises a heater disposed in a rearward direction of the mirror to heat the mirror.

The door may further include: an outer frame of which a front surface is provided therein with the mirror; and an inner frame of which a front surface is coupled with the mirror, a rear surface is coupled with the outer frame, and disposed in a forward direction of the heater, and a light source to create and irradiate light to the mirror. The outer frame may include: an inner frame mounting part configured to mount the inner frame; and a stiffness reinforcing part disposed at an outer edge of the inner frame mounting part and formed therein with a stiffness reinforcing rib. A light source mounting part may be formed at one side of the stiffness reinforcing part so that the light source is inserted and mounted in the light source mounting part. The stiffness reinforcing rib and the light source mounting part may formed therein with first wiring holes through which an electric wire of the light source passes. The stiffness reinforcing rib may be formed therein with a first wiring hole through which an electric wire of the heater passes.

According to the first objective of the present disclosure, a mirror provided at a front surface of a door may be dehumidified and defrosted by heat generated from a heater provided in the door.

According to the second objective of the present disclosure, wiring of a light source installed in the door is easily processed through first wiring holes formed in a stiffness reinforcing rib and a light source mounting part, and wiring of a heater is easily processed through a second wiring hole formed in the stiffness reinforcing rib.

Those skilled in the art will appreciate that the present disclosure may be carried out in specific ways other than those set forth herein without departing from the spirit and essential characteristics of the present disclosure. The above embodiments are therefore to be construed in all aspects as illustrative and not restrictive. The scope of the disclosure should be determined by the appended claims and their legal equivalents, not by the above description, and all changes coming within the meaning and equivalency range of the appended claims are intended to be embraced therein.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A bathroom management apparatus comprising:
a cabinet having a front side that is open;
a door configured to open/close the open front side of the cabinet;
a mirror provided at a front surface of the door; and
a heater configured to heat the mirror,
wherein the heater disposed behind the mirror to heat the mirror,
wherein the door includes:
   an outer frame having a front surface coupled to the mirror, and
   an inner frame having a front surface coupled to the mirror and a rear surface coupled to the outer frame, the inner frame being disposed adjacent to the heater,
wherein the front surface of the outer frame includes:
   an inner frame mounting region to accommodate the inner frame, and
   a stiffness reinforcing region disposed to surround an outer edge of the inner frame mounting region and having a plurality of stiffness reinforcing ribs.

2. The bathroom management apparatus of claim 1, wherein the inner frame has an opening to accommodate the heater.

3. The bathroom management apparatus of claim 1, wherein the door includes an insulation plate disposed between the heater and the outer frame.

4. The bathroom management apparatus of claim 1, wherein the plurality of stiffness reinforcing ribs includes
   a first stiffness reinforcing rib having a square shape and provided adjacent to the edge of the inner frame to surround the inner frame,
   a second stiffness reinforcing rib spaced apart from the first stiffness reinforcing rib to surround the first stiffness reinforcing rib,
   a third stiffness reinforcing rib spaced apart from the second stiffness reinforcing rib to surround the second stiffness reinforcing rib,
   a plurality of fourth stiffness reinforcing ribs provided at four corners of the outer frame to extend diagonally, each of the plurality of fourth stiffness reinforcing rib provided to connect respective corners of the first stiffness reinforcing rib, the second stiffness reinforcing rib, the third stiffness reinforcing rib, and an outer peripheral portion of the stiffness reinforcing region;
   a plurality of fifth stiffness reinforcing ribs provided to extend vertically to connect the first stiffness reinforcing ribs, the second stiffness reinforcing ribs, the third stiffness reinforcing rib, and the outer peripheral portion, wherein the plurality of fifth stiffness reinforcing ribs are provided a prescribed distance away from the four corners; and
   a plurality of sixth stiffness reinforcing ribs provided to extend vertically to connect the first stiffness reinforcing ribs, the second stiffness reinforcing ribs, the third stiffness reinforcing rib, and the outer peripheral portion, wherein the plurality of sixth stiffness reinforcing ribs are provided at the four corners.

5. The bathroom management apparatus of claim 4, wherein the inner frame includes a seventh stiffness reinforcing rib having a square shape that surrounds an opening provided in the inner frame,
   a plurality of eighth stiffness reinforcing ribs provided to extend radially to and connected to the seventh stiffness reinforcing rib and an outer peripheral portion of the inner frame, and
   a plurality of ninth stiffness reinforcing ribs provided between the seventh stiffness reinforcing rib and the outer peripheral portion, the plurality of ninth stiffness reinforcing ribs extending laterally at a top side and a bottom side of the inner frame.

6. The bathroom management apparatus of claim 4, wherein the plurality of first stiffness reinforcing ribs are disposed concentrically to the plurality of second stiffness reinforcing ribs and the plurality of third stiffness reinforcing ribs.

7. The bathroom management apparatus of claim 6, wherein the second stiffness reinforcing ribs are provided at a prescribed distance away from the first stiffness reinforcing ribs and the third stiffness reinforcing ribs.

8. The bathroom management apparatus of claim 4, wherein the plurality of stiffness reinforcing ribs are formed to have a same height relative to the front surface of the outer frame.

9. The bathroom management apparatus of claim 4, wherein the door includes
   a light source to irradiate light to the mirror, and
   a light source mounting part formed at one side of the stiffness reinforcing region so that the light source is inserted and mounted in the light source mounting part,
   wherein the light source mounting part is disposed at a central region of the stiffness reinforcing region at least one of an upper end or a lower end of the outer frame.

10. The bathroom management apparatus of claim 1, wherein the door includes a light source that irradiates light to the mirror, and
   a light source mounting part is formed at one side of the stiffness reinforcing region so that the light source is inserted and mounted in the light source mounting part.

11. The bathroom management apparatus of claim 10, wherein the plurality of stiffness reinforcing ribs and the light source mounting part are formed to include first wiring holes through which an electric wire of the light source passes.

12. The bathroom management apparatus of claim 1, wherein the plurality of stiffness reinforcing ribs is formed to include a first wiring hole through which an electric wire of the heater passes.

13. The bathroom management apparatus of claim 1, wherein an inner frame boss is formed at the inner frame, and
   the outer frame is formed to include an inner frame locking hole configured to be attached to the inner frame boss by a screw.

14. The bathroom management apparatus of claim 1, further comprising:
   a frame installed at an inner side of the cabinet to reinforce stiffness of the cabinet; and
   a hinge configured to rotatably couple the door with the frame,
   wherein the outer frame includes a hinge locking hole configured to interlock with the hinge.

* * * * *